United States Patent [19]
Soloman

[11] Patent Number: 5,900,634
[45] Date of Patent: May 4, 1999

[54] REAL-TIME ON-LINE ANALYSIS OF ORGANIC AND NON-ORGANIC COMPOUNDS FOR FOOD, FERTILIZERS, AND PHARMACEUTICAL PRODUCTS

[76] Inventor: Sabrie Soloman, 31 N. Monroe St., Ridgewood, N.J. 07450

[21] Appl. No.: 08/635,773

[22] Filed: Apr. 22, 1996

Related U.S. Application Data

[63] Continuation-in-part of application No. 08/338,909, Nov. 14, 1994.

[51] Int. Cl.$^6$ .................................................. G01J 5/02
[52] U.S. Cl. ........................... 250/339.11; 364/498
[58] Field of Search ................ 250/339.11; 356/346; 395/25; 364/498

[56] References Cited

U.S. PATENT DOCUMENTS

| | | | |
|---|---|---|---|
| 4,915,827 | 4/1990 | Rosenthal | 250/339.12 |
| 5,015,856 | 5/1991 | Gold | 250/339 |
| 5,095,459 | 3/1992 | Ohta et al. | 395/25 |
| 5,097,653 | 3/1992 | Soloman . | |
| 5,218,529 | 6/1993 | Meyer et al. | 364/413.01 |
| 5,239,180 | 8/1993 | Clarke | 250/339 |
| 5,267,151 | 11/1993 | Ham et al. | 364/413.09 |
| 5,278,412 | 1/1994 | DeThomas et al. | 250/339.11 |
| 5,363,968 | 11/1994 | Soloman . | |
| 5,369,940 | 12/1994 | Soloman . | |
| 5,370,754 | 12/1994 | Soloman . | |
| 5,448,069 | 9/1995 | Tobler et al. | 250/339.11 |
| 5,530,551 | 6/1996 | Cantrall et al. | 356/394 |

*Primary Examiner*—David P. Porta
*Assistant Examiner*—David Vernon Bruce
*Attorney, Agent, or Firm*—Kane, Dalsimer, Sullivan, Kurucz, Levy, Eisele and Richard, LLP

[57] ABSTRACT

The device is an apparatus for infrared spectroscopy. A succession of collimated light beams throughout the middle and near infrared spectrum are impinged against a sample or samples and the diffuse component of the reflected light is measured throughout the spectrum. This diffuse component is analyzed by a neural network to determine such characteristics as content of the sample.

6 Claims, 2 Drawing Sheets

REAL-TIME ON-LINE ANALYSIS OF ORGANIC AND NON-ORGANIC COMPOUNDS FOR FOOD, FERTILIZERS, AND PHARMACEUTICAL PRODUCTS

This application is a continuation-in-part application of application Ser. No. 08/338,909 filed on Nov. 14, 1994, entitled "Non-Destructive Identification of Tablet Dissolution by Means of Infrared Spectroscopy Analysis Measuring Hardness".

BACKGROUND OF THE INVENTION

1. Field of the Invention

The invention pertains to infrared spectroscopy with neural network analysis and associated quantitative methodology to analyze the contents of organic and non-organic products in the food, pharmaceutical, petroleum, soil and other industries.

2. Description of the Prior Art

Several spectroscopy systems have been developed to analyze the chemical compounds of organic and non-organic substances. The use of absorbed or reflected light energy in various spectral bands has been used to obtain spectral identification of the organic compounds. The time involved to perform the spectral analysis and the associated mathematical computation has been typically 45 to 180 seconds which has not been adequate for analysis of mass produced items, particularly while still on the production line, such as the determination of the content of a pharmaceutical product or the determination of fat, moisture and/or protein content in a meat or similar food product. Additionally, prior art spectroscopy techniques have not been able to detect minute quantities of potent substances in organic objects. Such increased sensitivity and accuracy would be of great use in the analysis of soil in the agricultural industry by determining which fertilizers have been used and what deficiencies the soil may have, and would have further similar application in the pesticide application industry by determining which pesticide has been used recently in an area thereby determining which pesticide has likely lost its efficacy.

OBJECTS AND SUMMARY OF THE INVENTION

It is therefore an object of this invention to provide an apparatus and method for infrared spectroscopy of organic compounds which can be performed sufficiently rapidly to be used on a mass production line in the pharmaceutical, food or similar industry.

It is therefore a further object of this invention to provide an apparatus and method for infrared spectroscopy of organic compounds which is sufficiently sensitive and accurate that agricultural soil can be tested for fertilizer content and nutrient deficiency.

It is therefore a still further object of this invention to provide an apparatus and method for infrared spectroscopy of organic compounds which is sufficiently sensitive and accurate that areas to which pesticides have been applied in the past can be analyzed for pesticide content.

The apparatus and method of the present invention uses a single plate permanently aligned self-compensating laser beam splitter which uses two input and two output optical ports and which yields an inherently symmetric interferogram required for object analysis. An interferometer sends infrared light which covers the range of 3800 to 11,500 wave numbers through a fiber optics cable to a probe. The light hits the object and some of the light is absorbed by the object and some of the light is reflected back to the probe. The relative absorption and reflectance throughout the infrared spectrum is dependent upon the chemical composition and physical characteristics of the sample. The spectrum of the reflected light therefore represents a "fingerprint" of the sample. The probe of the invention includes a filter element so that only the diffuse component of the reflected light and not the specular component of the reflected light is passed to the probe. This assures that the reflected light is representative of the chemical content of the sample rather than of the physical surface characteristics of the sample. The diffuse component of the reflected light is converted by a detector in communication with the probe into an electronic signal which is amplified and sent to a computer system. The software in the computer performs several transformations on the signal and displays the spectrum of the object.

An instantaneous decision to add or dilute certain soil compounds obtained from the present system can be linked to a global positioning system (GPS).

BRIEF DESCRIPTION OF THE DRAWINGS

Further objects and advantages of the invention will become apparent from the following description and claims, and from the accompanying drawings, wherein:

DETAILED DESCRIPTION OF THE PREFERRED EMBODIMENT

Figure 1:
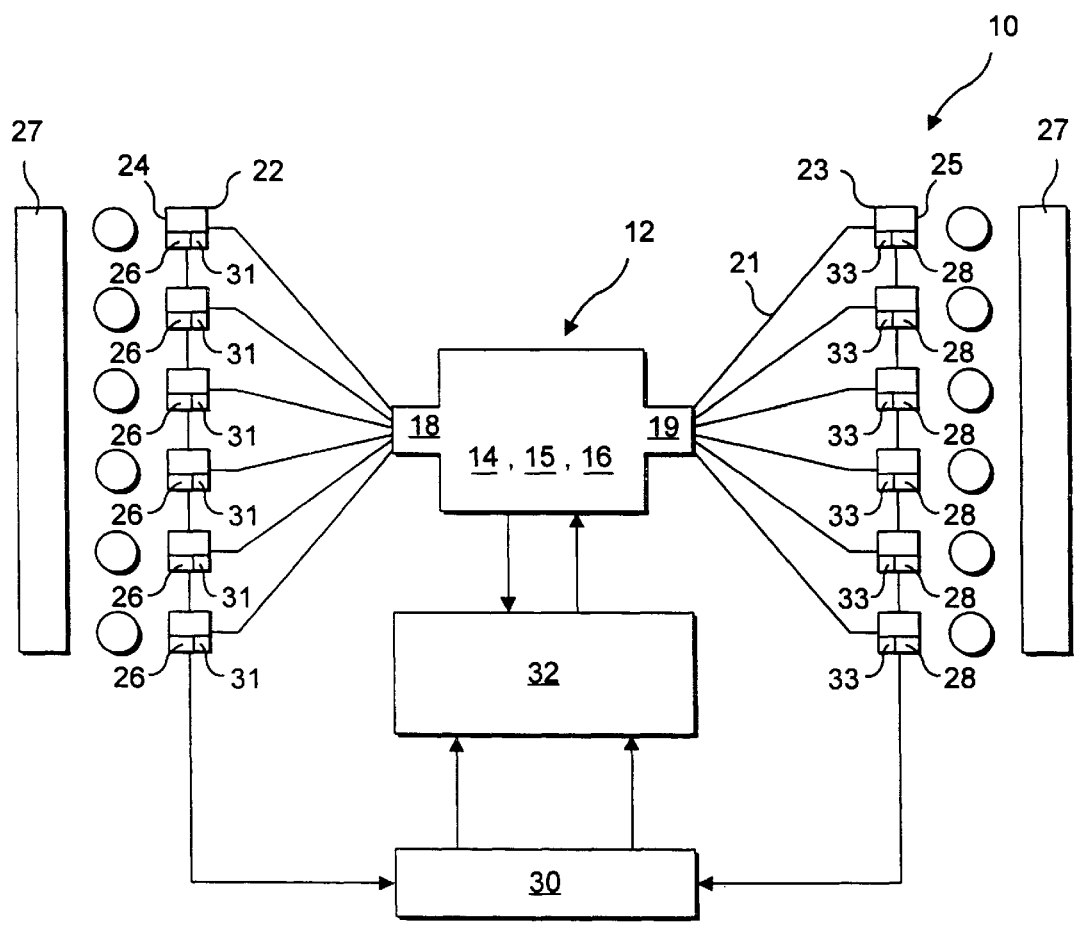
FIG. 1 is a schematic of the apparatus of the present invention.

Referring now to the drawings in detail wherein like numerals refer to like elements throughout the several views, one sees that FIG. 1 is a schematic of the infrared spectroscopy apparatus 10 of the present invention.

Interferometer 12 comprises an analyzer 14, a launcher 15, a laser measuring and adjustment system 16 and multiplexed heads 18, 19.

Interferometer 12 is typically hermetically sealed but is not vacuum or pressure tight. It is housed in a cast aluminum housing with upper and lower halves separated by a gasket and bolted together.

Analyzer 14 is equipped with an internal He-Ne laser reference for digital sampling and mirror velocity control. Digital sampling is synchronized by means of an error free up/down fringe counting using two references as fringe channels in quadrate. Analyzer 14 further includes a permanently mounted and aligned single plate beam-splitter with splitting and combining surfaces separated vertically to provide two input and two output beams of half the diameter of cube-corner mirrors. Analyzer 14 generates infrared light at various wavelengths, particularly in the middle and near infrared domain. Analyzer 14 communicates the light to laser measuring and adjustment system 16 which synchronizes the pulses of energy waves emitted at a specific interval of time. Launcher 15 collimates the light beam to a typical diameter of 0.25 mm. with a maximum beam divergence of 90 milliradians (full angle when beam stop is defined at the apex of the corner cube retroreflectors) and communicates the collimated light beam to multiplexed heads 18, 19 which are positioned on both ends of launcher 15. Multiplexed heads 18, 19 receive the collimated light beam from launcher 15 and communicates the collimated light beam to bundles of fiber optics 20, 21 (typically comprised of OH free quartz fibers on the order of two meters long), including dedicated branches. The dedicated branches of bundles of fiber optics 20, 21 communicate the collimated light beam to the plurality of probes 22, 23, respectively. In FIG. 1, six probes 22 and six probes 23 are illustrated, but the infrared spectroscopy apparatus 10 of the present invention can be similarly adapted to a different number of probes. Each of the probes 22, 23 simultaneously delivers a collimated light beam to an individual sample (that is, in the illustrated FIG. 1, twelve samples are analyzed simultaneously). The individual samples are communicated to the probes 22, 23 by a delivery and sorting mechanism 27 such as is used in an assembly line. Delivery and sorting mechanism 27 can further receive signals from computer system 32 to reject samples which have been judged defective by infrared spectroscopy apparatus 10. Additionally, the delivery and sorting mechanism 27 includes a sensor tracking system which detects the leading and trailing edge of the samples (synchronous production being triggered through one of three types of triggering mechanisms—analog level triggering, analog edge triggering, and digital edge triggering level) and an automatic closed loop mechanism to provide an optimum distance between the lens elements 24, 25 of probes 22, 23 and the samples. Different samples may require a different distance to the lens elements 24, 25 of probes 22, 23 depending upon the material characteristics of the sample. As the optimum distance between the sample and the probe lens depends upon the characteristics of the sample, an closed-loop automatic optimization of the distance between the probe lens and the sample is performed in conjunction with servo motors 31, 33 attached to probes 22, 23 in order to maximize the signal-to-noise ratio Reflected infrared light is received back to probes 22, 23 which include lens elements 24, 25, respectively, which include filtering characteristics to eliminate the specular component (i.e., surface reflections due to the physical characteristics of the external surface) of the reflected light. The diffuse component of the reflected light is passed to detectors 26, 28, with one detector 26, 28 typically associated with each probe 22, 23. Detectors 26, 28 are typically indium-arsenate (InAs) or MCT detectors which receive the reflected light energy and create an electronic response proportional to the amount of energy reflected or absorbed by the sample. Detectors 26, 28 can be a 1.0 mm. diameter DTGS detector module, complete with matched preamplifier. Detectors 26, 28 are optimized for inspection application of samples varying in length from 4 mm to 15 mm. High sensitivity and linearity are required for high speed data analysis. The diffuse component of the reflected light is thereby converted by detectors 26, 28 into an electric signal which is sent to electronic module 30. Electronic module 30 amplifies the response signals from the detectors 26, 28 and communicates the amplified signal to computer system 32.

Computer system 32 is typically implemented as a dual processor and/or PENTIUM-PRO® system with standard features such as a keyboard, monitor, high-capacity hard-drive, CD-ROM drive, adequate random access memory to run software, including a neural network, on a WINDOWS-NT® or WINDOWS-95® platform, and a compatible, preferably color, printer.

The software of the computer system 32 preferably is a fully integrated data collection permitting operation of most types of interferometers including such tools as partial least square quantitative analysis, interactive subtraction, spectrum data base and data base search, neural networks for spectral analysis, Fourier domain smoothing, curve fitting, polynomial baseline correction, three-dimensional graphics capabilities, rapid multi-spectral data acquisition, area calculations, separate production menus for supervisors and operators, upper and lower control limit charts, upper and lower working control limit charts and audio-visual warning signals. Additionally, the software preferably includes all of the algorithms described in parent application Ser. No. 08/338,909 filed on Nov. 14, 1994, entitled "Non-Destructive Identification of Tablet Dissolution by Means of Infrared Spectroscopy Analysis Measuring Hardness", the contents of which are hereby incorporated by reference. Additionally, the algorithm associating the integral of the reflected infrared spectrum with the hardness, dissolution and disintegration of the sample along with Sabrie's index are implemented as follows: A=Area of Spectrum= $\int_{\lambda_1}^{\lambda_2} a(\lambda) d\lambda$ where $\lambda$=wavelength of light in near or mid-infrared range $\lambda_1, \lambda_2$=limits of wavelength $\lambda$ $a(\lambda)$=the absorbency as a function of $\lambda$ H=hardness D=dissolution DI=disintegration $H=c_1 A+c_2$ $c_1, c_2$=constants of linearity $D=d_1 A+d_2$ $d_1, d_2$=constants of linearity $DI=e_{0 \to 1} D$ where $e_{0 \to 1}$ may be considered a dissolution factor if $e_{0 \to 1}=1$, the disintegration becomes dissolution if $e_{0 \to 1}=0$, the material becomes indissoluble Computer system 32 further includes a data acquisition system on a single board which is capable of acquiring data at a rate of 1,000,000 to 12,000,000 samples per second. The data acquisition system includes scan velocity control with two selectable scan velocities selected via a switch on the detector amplifier board; variable scan length logic for variable resolution; a true 12-bit analog to digital converter with built-in sample and hold; and byte parallel data transmission. The data transmission from the electronic module 30 to the computer system 32 is unidirectional whereby the analyzer 14 does not require any commands from the computer. All scanned data is synchronous with previous scans, which permits direct co-adding of spectral data.

The various elements of interferometer 12 generate a sequential series of laser beams of different frequencies throughout the near and middle infrared spectrum. These laser beams of different frequencies strike the samples and the diffuse reflected infrared light is detected by detectors 26, 28. The resulting electronic signals are amplified by electronic module 30 and sent to computer system 32 where the signals are converted into spectrum S. It is assumed that spectrum S of the sample is comprised of weighted percentages $w_i$ of the various spectra $S_i$ of various known elements in the data base. In other words:

$$S=w_1 S_1+w_2 S_2+w_3 S_3+w_4 S_4$$

where $S_1$ is the spectrum (i.e., a function of wavelength, not a single point) of component i in the data base, and $w_i$ is the percentage, value or function (i.e., the unknown quantities to be solved for) of the respective component i within the sample.

Figure 2:
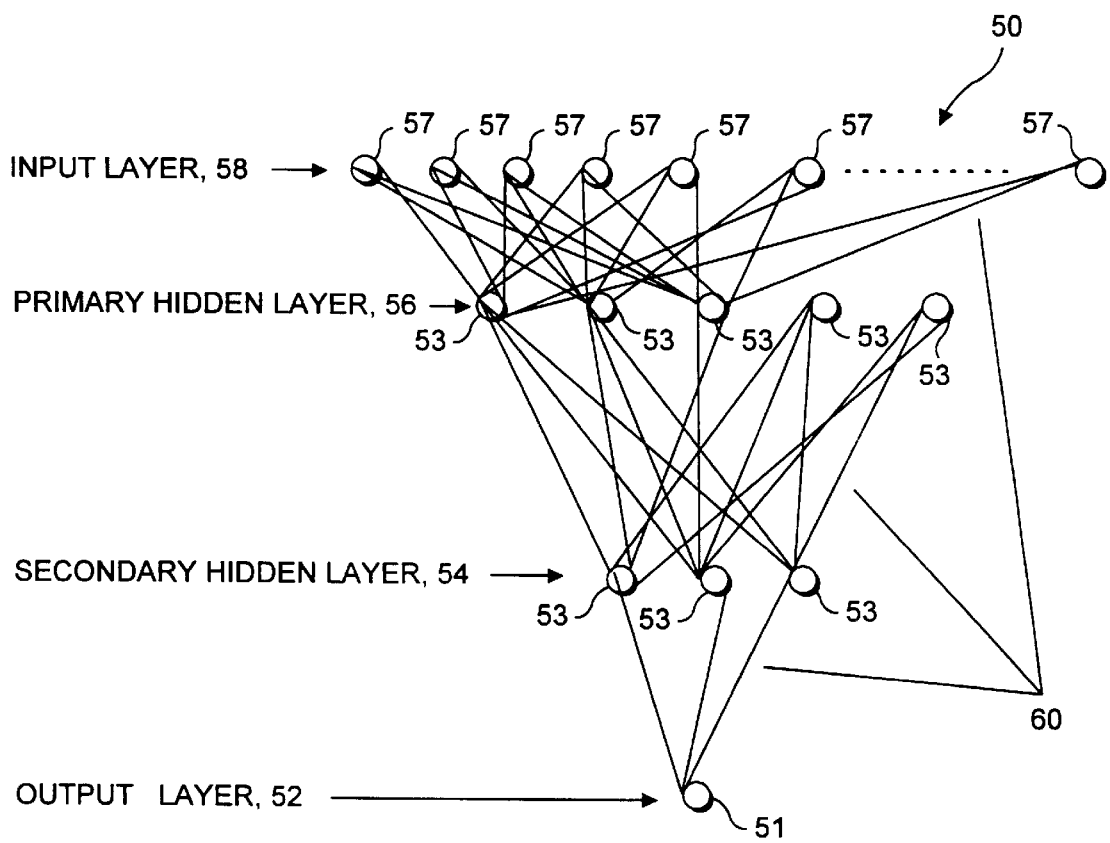
FIG. 2 is a schematic of the neural network of the present invention.

Rather than perform an unwieldy simultaneous equation calculation, a neural network algorithm implemented by computer system 32 is used as a "transformation function" to map the input into a useful output, that is, to solve for the various percentages, values or functions $w_i$. The transformation function of the neural network is obtained by training the network using a large number of samples for which both the spectrum (input) and the characteristics of the objects (output) based on the reflected spectrum are given. As shown in FIG. 2, neural networks 50 include processing elements (Pes or neurons) which include the node(s) 51 of output layer 52 (representing object characteristics in spectroscopy), the nodes 53 of secondary and primary hidden layers 54, 56 and the nodes 57 of input layer 58 (representing the spectrum in spectroscopy), and weighted connections 60 between the various successive layers of nodes.

A typical application would include 341 processing elements or nodes 57 in input layer 58 representing the energy wavelengths spaced from 11,800 to 3,500 wave numbers. At each processing element 57, there is a value representing the energy absorbency at each specific wave number. A typical application would further include five nodes 53 in primary hidden layer 56 imperative to transform the inputs to reach meaningful outputs. A typical application would further include three nodes 53 in secondary hidden layer 54 to transform the inputs from all layers above to reaching meaningful outputs. A typical application would further include a single node 51 in its output layer 52 for each required output variable.

Neural networks are a very useful tool in spectroscopy for the following reasons:
1. the number of points in the spectrum is usually very large (greater than 300) while the number of characteristics is usually relatively small (usually less than 4);
2. the mapping between the spectrum and the desired characteristics is usually not simple and most often it is non-linear;
3. since the present apparatus is designed to be used in real-time productions, decisions must be made in a very short time. Neural networks are among the fastest available spectroscopy tools; and
4. although preparing a training set for the neural network may take a long time and involve substantial effort, it is usually less effort than the effort required to derive the mapping, come up with an algorithm for the mapping and write a specialized computer code for the algorithm.

To perform spectral analysis using neural networks, the following steps are required—creating a training set; generating a neural network; training the neural network using the training set; and using the network to find the characteristics of a sample.

The training set spectra must be representative of the actual spectra that the neural network will be used to analyze and identify. For instance, if the network is going to be used with spectra which consist of only one scan, then the neural network should be trained with spectra consisting of one scan. In order for the network to operate properly, most of the variations in the spectra of the object must be present in the training set. This usually requires at least 6 to the "Nth" power spectra in the training set where "N" is equal to the number of output characteristics.

The accuracy of the neural network depends on the accuracy of the training set. Even if one spectrum of the training set is wrong (for instance, the sample was not correctly placed under the probe, the spectrum does not correspond to the specified output or a wrong object is scanned, etc.) then the output of the entire network will be unusable. Therefore, during the training session, it is extremely important to visually check each spectrum for accuracy, consistency and noise. The system is developed to protect against unusual input data (spectrum), a display message is designed to indicate the sample number with the most error is occurring for correction, if required.

The various samples in the training set are scanned and the known output characteristics are manually entered by the operator. By methods known to the science of neural networks, the neural network 50 then calculates or maps the various weighted connections 60 in order to provide the transformation function required in the analysis of unknown samples.

In order for the neural network to be able to generalize the mapping that it learns from the training set, the network must be stopped from learning after the average and maximum learning errors reach acceptable values. If the network is allowed to learn until the maximum and average learning errors reach arbitrary small values, then the network will learn the training set exactly but will not be able to generalize beyond the training set.

In order to use the infrared spectroscopy apparatus 10 of the present invention, a user first programs or "trains" the neural network 50 as described above. Then the user provides samples via the delivery and sorting mechanism 27 to the various probes 22, 23. The probes 22, 23 are then supplied with a sequence of collimated light beams of various frequencies throughout the middle and near infrared spectrum from interferometer 12 via fiber optics 20, 21. The reflected infrared light is detected by detectors 26, 28 and a corresponding electrical signal is generated which is amplified by electronic module 30 and subsequently communicated to computer system 32 where various algorithms including those of the neural network 50 are performed to calculate the various characteristics of the samples. If the characteristics are out-of-range, then delivery and sorting mechanism can eliminate the defective samples from the production lines.

Alternately, for non-production line applications, such as finding the soil content or the pesticide presence, the various concentrations can be displayed to the user via the screen of computer system 32.

Thus the several aforementioned objects and advantages are most effectively attained. Although a single preferred embodiment of the invention has been disclosed and described in detail herein, it should be understood that this invention is in no sense limited thereby and its scope is to be determined by that of the appended claims.

What is claimed is:
1. An infrared spectroscopy apparatus including:
   means for generating a succession of collimated light beams throughout a frequency spectrum in the near and middle infrared range;
   a plurality of probes associated with a respective plurality of samples, said plurality of probes for impinging said succession of collimated light beams against the respective plurality of samples;

a delivery and sorting means for transporting the plurality of samples;

means for measuring reflected light from the plurality of samples in response to said succession of collimate light beams thereby generating a reflected spectrum; and a neural network means for analyzing said reflected spectrum thereby determining contents of the plurality of samples.

2. The infrared spectroscopy apparatus of claim 1 wherein said collimated light beams are communicated to said plurality of probes via a fiber optic means.

3. The infrared spectroscopy apparatus of claim 2 wherein said plurality of probes are of indium-arsenate construction.

4. The infrared spectroscopy apparatus of claim 2 wherein said means for measuring reflected light includes means for rejecting specular reflected light.

5. The infrared spectroscopy apparatus of claim 2 wherein said delivery and sorting means is associated with a production line.

6. The infrared spectroscopy apparatus of claim 5 wherein said delivery and sorting means includes means for rejecting samples responsive to said neural network means.

\* \* \* \* \*